(12) United States Patent
Okino et al.

(10) Patent No.: US 6,258,581 B1
(45) Date of Patent: Jul. 10, 2001

(54) CERAMIDASE GENE

(75) Inventors: Nozomu Okino; Makoto Ito, both of Fukuoka (JP)

(73) Assignee: Takara Shuzo Co., Ltd., Kyoto-fu (JP)

( * ) Notice: Subject to any disclaimer, the term of this patent is extended or adjusted under 35 U.S.C. 154(b) by 0 days.

(21) Appl. No.: 09/328,501

(22) Filed: Jun. 9, 1999

(30) Foreign Application Priority Data

Aug. 20, 1998 (JP) .................................. 10-234769

(51) Int. Cl.[7] .............................. C12N 9/14; C12N 1/20; C12N 15/00; C07H 21/04; C07K 1/00
(52) U.S. Cl. .................. 435/195; 435/252.3; 435/320.1; 536/23.2; 530/350
(58) Field of Search .................. 435/195, 252.3, 435/320.1; 536/23.2; 530/350

(56) References Cited

FOREIGN PATENT DOCUMENTS 1014563  1/1998 (JP) .

OTHER PUBLICATIONS

Suggs et al. PNAS 78 (11), 6613–6617, 1981.*
Edman et al. Eur. J. Biochem. 1 : 80–91, 1967.*
N. Okino et al., Purif. and Char. of a Novel Ceramidase from Pseudomonas aeruginosa, The Journal of Biol. Chem., vol. 273, Jun. 5, 1998, pp. 14368–14373.
Jurgen Koch et al., Molecular Cloning and Characterization of a Full–length Complementary DNA Encoding Human Acid Ceramidase, The Journal of Biological Chemistry, vol. 271, No. 51, Dec. 20, 1996, pp. 33110–33115.
Chi–Ming Li et al., Cloning and Characterization of the Full–Length cDNA and Genomic Sequences Encoding Murine Acid Ceramidase, Genomics 50, (1998), pp. 267–274.

* cited by examiner

*Primary Examiner*—Ponnathapu Achutamurthy
*Assistant Examiner*—Tekchand Saidha
(74) *Attorney, Agent, or Firm*—Birch, Stewart, Kolasch & Birch, LLP

(57) ABSTRACT

To provide a polypeptide having ceramidase activity, and a gene encoding thereof useful as an reagent for lipid engineering and as indices for diagnosis of atopic dermatitis, an easy method for detecting the polypeptide and method for detecting the gene as well as a method for detecting atopic dermatitis. A polypeptide having an amino acid sequence as shown in SEQ ID NO: 1 in Sequence Listing, or a polypeptide having an amino acid sequence which has substitution, deletion, addition or insertion of one or more amino acids in the amino acid sequence of SEQ ID NO: 1 and having ceramidase activity; a gene encoding the polypeptide; a gene capable of hybridizing with the above genes under stringent conditions, and encoding a polypeptide having ceramidase activity; an oligonucleotide probe or primer, which is capable of hybridizing under stringent conditions with the above genes or with a gene having a nucleotide sequence complementary thereto; a method for detecting a gene encoding a polypeptide having ceramidase activity, by using the oligonucleotide probe and/or primer; an antibody or a fragment thereof, which is capable of specifically binding to the polypeptide; a method for detecting a polypeptide having ceramidase activity, by using the above antibody or fragment thereof; a method for detecting atopic dermatitis, by the methods.

7 Claims, 1 Drawing Sheet

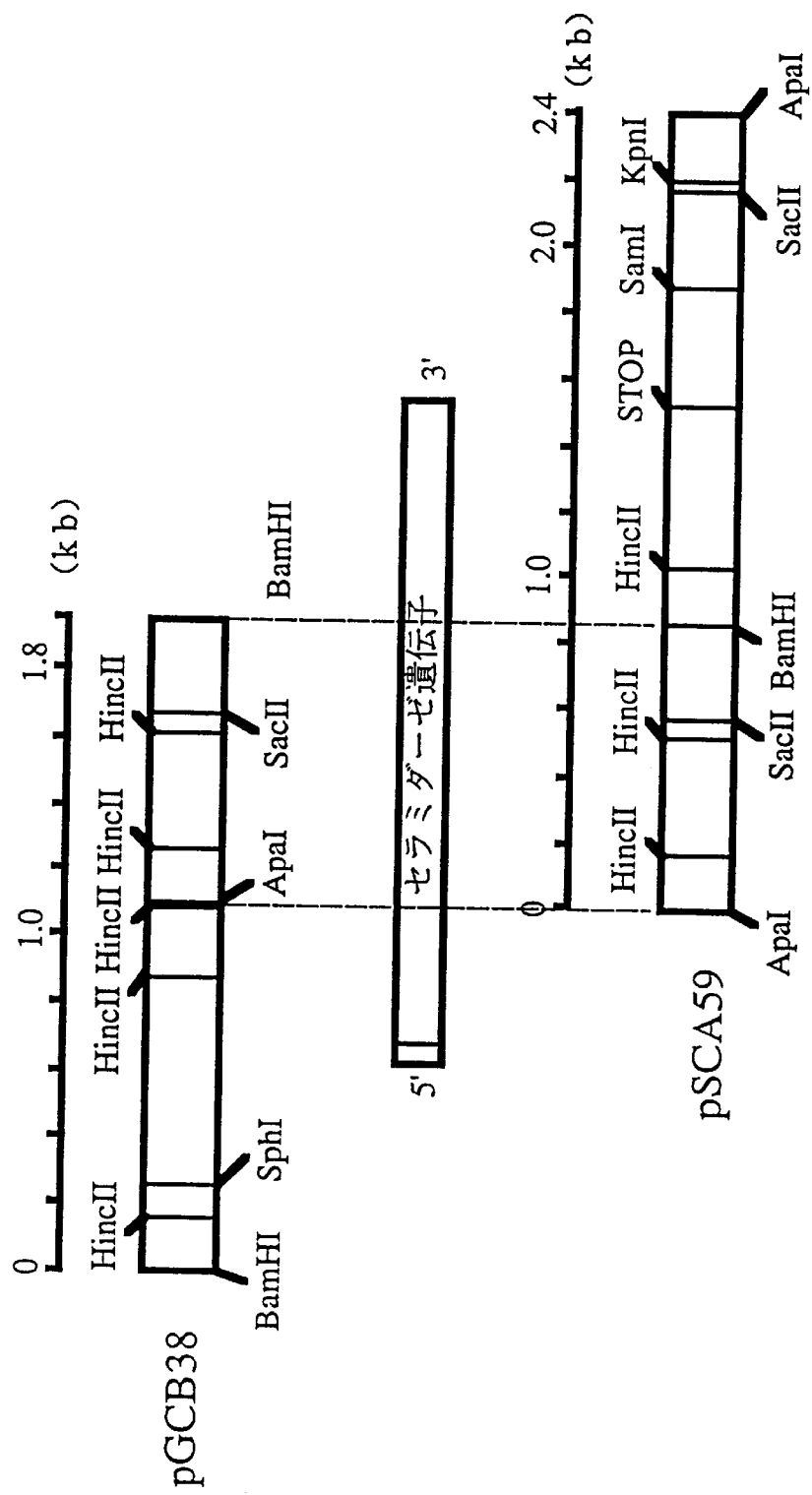
F I G. 1

CERAMIDASE GENE

BACKGROUND OF THE INVENTION

1. Field of the Invention

The present invention relates to a polypeptide having ceramidase activity, and a gene encoding said polypeptide. More particularly, the present invention relates to an amino acid sequence of ceramidase as well as a nucleotide sequence encoding the amino acid sequence which are useful as an reagent for lipid engineering for analyzing structure and action of ceramide and as an index for diagnosis of atopic dermatitis. In addition, the present invention relates to a method for producing a polypeptide having ceramidase activity by gene engineering. Further, the present invention relates to a method for detecting the polypeptide, and a method for detecting a gene encoding the polypeptide. Further, the present invention relates to a method for detecting atopic dermatitis by utilizing the above method for detecting the polypeptide and the above method for detecting the gene.

2. Discussion of the Related Art

Ceramidase is an enzyme that hydrolyses ceramide, which is one of sphingolipids, into sphingosine and a fatty acid. Sphingosine formed by hydrolysis of ceramide by ceramidase has various physiological activities, such as inhibition of protein kinase C, activation of phospholipase D, inhibition of a calmodulin-dependent enzyme, and the like, and is an important substance which is considered to have a role in regulating cellular functions through its involvement in cell proliferation and intracellular signal transduction. The regulation of the level of such sphingosine is an important role played by ceramidase.

Ceramidases are classified on the basis of its optimum pH into an acidic ceramidase and a neutral/alkaline ceramidase. There have been reported that ceramidases having optimum pH in an acidic region are present in mammalian tissues such as rat brain [*Biochemistry*, 8, 1692–1698 (1969)], guinea pig epithelial cell [*J. Biol. Chem.*, 270, 12677–12684 (1995)], human kidney [*Biochim. Biophys. Acta*, 398, 125–131 (1975)], spleen [*Biochim. Biophys. Acta*, 1004, 245–251 (1989)], fibroblast [*Biochem. J.*, 205, 419–425 (1982)] and epithelium [*FEBS Lett.*, 268, 110–112 (1990)]; human urine [*J. Biol. Chem.*, 270, 11098–11102 (1995)], and the like.

Among these ceramidases, the amino acid sequences and the nucleotide sequences of ceramidase purified from human urine have been determined [*J. Biol. Chem.*, 271, 33110–33115 (1996)]. Utilizing the homology with this gene, a ceramidase gene of a mouse has also been obtained [*Genomics*, 50, 267–274 (1998)]. However, all these are acidic ceramidases derived from mammals, and no amino acid sequences or nucleotide sequences of neutral/alkaline ceramidase or of ceramidases derived from microorganisms have yet been determined.

On the other hand, a ceramidase-producing microorganism is known to be present on the epidermis of lesion of atopic dermatitis, and this enzyme is suggested to be causative of or be involved in the exacerbation of atopic dermatitis. However, this enzyme is ceramidase of which optimum pH is within an alkaline region (hereinafter referred to as alkaline ceramidase) [*J. Biol. Chem.*, 273, 14368–14373 (1998)].

When a naturally-occurring ceramidase is produced from a ceramidase-producing microorganism, it is necessary to add an expensive sphingolipid to a culture medium in order to induce the production of an enzyme, and in purification step, it is necessary to separate and remove the remaining sphingolipid or a degradation product thereof from a fraction containing ceramidase. In addition, since enzymes other than ceramidases such as sphingomyelinase are simultaneously produced during the culture, it is difficult to isolate and purify only a desired ceramidase from these enzymes. Moreover, the amino acid sequences or the gene structures of microorganism-derived alkaline ceramidase are completely unknown, so that the method for producing ceramidase by gene engineering cannot be utilized.

Furthermore, although the presence of the ceramidase-producing microorganism is expected to be used as an index for diagnosing atopic dermatitis and as a method for confirming a therapeutic effect, no means for simply detecting or identifying such a microorganism has yet been known. Conventional methods have necessitated extremely complicated processes that the microorganism is isolated and then cultured, and thereafter its ceramidase activity is assayed. Thus, a method for producing a high-purity ceramidase derived from microorganisms at a lower cost is desired as well as a method for detecting a ceramidase-producing microorganism in a simple, non-time-consuming procedure.

SUMMARY OF THE INVENTION

A first object of the present invention is to provide a polypeptide having ceramidase activity. A second object of the present invention is to provide a gene encoding the above polypeptide. A third object of the present invention is to provide a transformant harbouring the above gene. A fourth object of the present invention is to provide a production method capable of easily and massively producing high-purity ceramidase utilizing the above transformant. A fifth object of the present invention is to provide an oligonucleotide probe or a primer capable of specifically hybridizing with the gene of the present invention. A sixth object of the present invention is to provide an antibody or a fragment thereof, which is capable of specifically binding to a polypeptide of the present invention. A seventh object of the present invention is to provide a method for detecting a ceramidase gene by using the oligonucleotide probe or the primer of the present invention. An eighth object of the present invention is to provide a method for detecting ceramidase by using the antibody or the fragment thereof of the present invention, and a kit used therefor. Furthermore, a ninth object of the present invention is to provide a method for detecting atopic dermatitis by utilizing a method for detecting the ceramidase gene or method for detecting ceramidase of the present invention.

As a result of intensive investigation in order to isolate a gene encoding a polypeptide having ceramidase activity, the present inventors have succeeded in isolation of a gene encoding a polypeptide having ceramidase activity and elucidation of the nucleotide sequence of the gene. In addition, based on such findings, the present inventors have established a method capable of easily and massively producing high-purity ceramidase; a method for detecting a polypeptide having ceramidase activity; and a method for detecting the ceramidase gene, and the present invention has been completed thereby. In addition, the correlation between such ceramidase and atopic dermatitis has been found, whereby a method for simply detecting atopic dermatitis has been able to be established.

Specifically, the gist of the present invention follows:

[1] a polypeptide having an amino acid sequence as shown in SEQ ID NO: 1 in Sequence Listing, or a polypeptide having an amino acid sequence which has substitution, deletion, addition or insertion of one or more amino acids in the amino acid sequence of SEQ ID NO: 1 and having ceramidase activity;

[2] a gene encoding the polypeptide of the above item [1];

[3] the gene according to the above item [2], wherein the gene has a nucleotide sequence as shown in SEQ ID NO: 2 in Sequence Listing, or a nucleotide sequence which has substitution, deletion, addition or insertion of one or more bases in the nucleotide sequence of SEQ ID NO: 2 and encodes a polypeptide having ceramidase activity;

[4] a gene capable of hybridizing with the gene of the above item [2] under stringent conditions, and encoding a polypeptide having ceramidase activity;

[5] a transformant harbouring the gene of the above item [2];

[6] a method for producing a polypeptide having ceramidase activity, comprising culturing the transformant of the above item [5], and collecting a polypeptide having ceramidase activity from the resulting culture;

[7] an oligonucleotide probe or a primer, which is capable of hybridizing under stringent conditions with the gene of the above item [2] or with a gene having a nucleotide sequence complementary thereto;

[8] a method for detecting a gene encoding a polypeptide having ceramidase activity, by using the oligonucleotide probe and/or the primer of the above item [7];

[9] a kit for detection of a gene encoding a polypeptide having ceramidase activity, comprising the oligonucleotide probe and/or the primer of the above item [7];

[10] an antibody or a fragment thereof, which is capable of specifically binding to the polypeptide of the above item [1];

[11] a method for detecting a polypeptide having ceramidase activity, by using the antibody or the fragment thereof of the above item [10];

[12] a kit for detection of a polypeptide having ceramidase activity, comprising the antibody or the fragment thereof of the above item [10];

[13] a method for detecting atopic dermatitis, comprising detecting a gene encoding a polypeptide having ceramidase activity by the method of the above item [8]; and

[14] a method for detecting atopic dermatitis, comprising detecting a polypeptide having ceramidase activity by the method of the above item [11].

BRIEF DESCRIPTION OF THE DRAWING

FIG. 1 shows a restriction endonuclease map for DNA insert of plasmids pSCA59 and pGCB38.

DETAILED DESCRIPTION OF THE INVENTION (1) Polypeptide Having Ceramidase Activity In the present invention, the term "ceramidase" refers an enzyme having activity for hydrolyzing ceramide into sphingosine and a fatty acid as mentioned above.

Ceramidase activity can be determined according to a method described in, for example, *Journal of Biological Chemistry*, 273, 14368–14373 (1998).

In the present invention, an origin of ceramidase includes, but not particularly limited to, for example, ceramidases derived from microorganisms, such as bacteria, Actinomycetes, yeasts, filamentous fungi, Ascomycetes and basidiomycetes; or ceramidases derived from organisms, such as plants, animals and insects. Concretely, for instance, *Pseudomonas aeruginosa* strain AN-17, isolated from skin of patients with atopic dermatitis is preferred as a source for obtaining the ceramidase of the present invention. An amino acid sequence of the ceramidase derived from the above strain is shown in SEQ ID NO: 1 in Sequence Listing. The above strain AN-17 is deposited under accession number FERM P-15699 with the National Institute of Bioscience and Human-Technology, Agency of Industrial Science and Technology, Ministry of International Trade and Industry [Address: 1–3, Higashi 1-chome, Tsukuba-shi, Ibaraki-ken Japan (postal code 305–8566)] since Jun. 26, 1996.

Incidentally, in the present specification, the term "polypeptide having ceramidase activity" (the polypeptide may be simply referred herein, as ceramidase) refers to a polypeptide having the amino acid sequence as shown in SEQ ID NO: 1 in Sequence Listing. The term "polypeptide having ceramidase activity" may further include not only a polypeptide having an amino acid sequence of naturally-occurring ceramidase but also a polypeptide having an amino acid sequence which has a mutation such as substitution, deletion, addition or insertion of one or more amino acids in the amino acid sequence as shown in SEQ ID NO: 1, as long as the polypeptide having an amino acid sequence which has a mutation is a polypeptide having the same level of ceramidase activity as determined by the method for determining activity as described the above. In addition, the polypeptide having an amino acid sequence may have two or more mutations, as long as the above mutation is a mutation whereby the resulting polypeptide has ceramidase activity. As described herein, "an amino acid sequence having a mutation" includes amino acid sequences in which a naturally-occurring mutation is introduced as well as those in which an artificial mutation is introduced.

(2) Ceramidase Gene

The ceramidase gene of the present invention refers to a gene encoding the above polypeptide having ceramidase activity, i.e. a nucleic acid having a nucleotide sequence encoding an amino acid sequence of a polypeptide having ceramidase activity. The ceramidase gene of the present invention includes, for example, a gene encoding ceramidase derived from the above *Pseudomonas aeruginosa* strain AN-17, of which nucleotide sequence is shown in SEQ ID NO: 2 in Sequence Listing. The ceramidase gene of the present invention also encompasses a gene encoding an amino acid sequence of a polypeptide having an amino acid sequence which has substitution, deletion, addition or insertion of one or more amino acids in the above amino acid sequence of naturally-occurring ceramidase, and having ceramidase activity.

The gene of the present invention also encompasses a gene having a nucleotide sequence which has substitution, deletion, addition or insertion of one or more bases in the nucleotide sequence as shown in SEQ ID NO: 2 in Sequence Listing and encodes a polypeptide having ceramidase activity.

As described herein, "nucleotide sequence which has substitution, deletion, addition or insertion" includes a nucleic acid sequence into which a naturally-occurring mutation is introduced or an artificial mutation is introduced.

Further, the gene of the present invention encompasses a gene capable of hybridizing with the above-mentioned ceramidase genes under stringent conditions, and encoding a polypeptide having ceramidase activity. Hybridization can be performed by a method described in e.g. *Molecular Cloning: A Laboratory Manual* 2nd ed., published by Cold Spring Harbor Laboratory in 1989, edited by T. Maniatis et al. The conditions for hybridization include, for instance, the conditions of incubation with a probe at 65° C. for overnight in a solution containing 6×SSC (composition of 1×SSC: 0.15 M NaCl, 0.015 M sodium citrate, pH 7.0), 0.5% SDS, 5×Denhardt's reagent, and 100 mg/ml herring sperm DNA.

Since the primary structure and the genetic structure of ceramidase are clarified by the present invention, there can be obtained a gene encoding a polypeptide having at least one of deletion, addition, insertion or substitution of one or more amino acid residues in an amino acid sequence of naturally-occurring ceramidase by means of introducing random mutation or site-specific mutation into the gene of the present invention, by which it is made possible to obtain genes encoding ceramidases which have ceramidase activity with slight differences in properties such as optimum temperature, stable temperature, optimum pH, and stable pH. In addition, there can be produced these ceramidases by gene engineering.

The method for introducing random mutation includes, for example, a method for causing transition mutation, in which cytosine base is converted into uracil base, by a chemical treatment with sodium hydrogensulfite [*Proc. Natl. Acad. Sci. U.S.A.*, 79, 1408–1412 (1982)]; a method for lowering fidelity of incorporation of nucleotides in DNA synthesis by carrying out PCR in a reaction mixture containing manganese [*Anal. Biochem.*, 224, 347–353 (1995)], and the like.

The method for introducing site-specific mutation includes, for example, a method utilizing amber mutation [gapped duplex method; *Nucleic Acids Res.*, 12, 9441–9456 (1984)]; a method utilizing a host in which genes dut (dUTPase) and ung (uracil-DNA glycosilase) are deleted [Kunkel method; *Proc. Natl. Acad. Sci. U.S.A.*, 82, 488–492 (1985)]; a method comprising carrying out PCR by utilizing amber mutation (WO98/02535), and the like. Various kits for introducing site-specific mutation into the desired gene by these methods are commercially available, and by utilizing the above kits, there can be easily obtained a gene in which a desired mutation is introduced.

A method for obtaining a microorganism-derived ceramidase gene by means of hybridization method will be described below.

1) First, a partial amino acid sequence of ceramidase is determined as information for preparing a probe for cloning a ceramidase gene. A purified ceramidase is subjected to conventional amino acid sequencing by Edman degradation without any treatment [*J. Biol. Chem.*, 256, 7990–7997 (1981)], or a purified peptide fragment isolated and purified from a peptide mixture obtained by limited hydrolysis by a highly substrate-specific proteolytic enzyme such as lysyl endopeptidase and N-tosyl-L-phenylalanyl chloromethyl ketone (TPCK)-tripsin is subjected to an amino acid sequencing. Based on the information of the partial amino acid sequence as elucidated above, an oligonucleotide to be used as a probe for hybridization is designed, and synthesized chemically.

2) Genomic DNA from a ceramidase-producing microorganism is prepared, digested completely with an appropriate restriction enzyme, separated by agarose gel electrophoresis, and then blotted on a nylon membrane by a usual method. The DNA fragment on the nylon membrane is hybridized with the synthetic oligonucleotide probe described above under generally employed conditions. For example, the nylon membrane is blocked in a pre-hybridization solution containing salmon sperm DNA and then incubated overnight together with a $^{32}$P-labeled synthetic oligonucleotide probe. After washing the nylon membrane, an autoradiogram is prepared, and a DNA fragment hybridizing with the synthetic oligonucleotide is detected.

3) A DNA fragment corresponding to signal on the autoradiogram is extracted and purified from the agarose gel. The DNA fragment thus obtained is incorporated into a vector such as a plasmid vector by a usually employed method to prepare a recombinant DNA molecule. The vector may be any of various commercially available vectors. Subsequently, the recombinant DNA molecule is introduced into an appropriate host such as *Escherichia coli* to obtain a transformant. The method of transformation may be a usually employed method such as one selected depending on a vector to be used from those described in the above *Molecular Cloning: A Laboratory Manual*, 2nd Ed., and the like.

4) Subsequently, a transformant harbouring a fragment of a ceramidase gene is screened. A screening method may be appropriately selected from colony hybridization, plaque hybridization and the like depending on the kinds of the vectors. There may also be employed PCR method using as a sample a colony or a plaque as it is, or a method employing an expression of ceramidase activity as an index.

5) A recombinant DNA molecule into which a fragment of a ceramidase gene is incorporated is prepared from a transformant harbouring the fragment, and the nucleotide sequence of the fragment is analyzed. The nucleotide sequence may be determined by a usual method such as dideoxy method. By comparing the nucleotide sequence thus determined with the partial amino acid sequence of the ceramidase obtained previously and the molecular weight of the ceramidase, there can be determined whether the DNA fragment obtained is the entire desired ceramidase gene, or a partial sequence thereof.

6) When the DNA fragment obtained does not contain the entire length of the ceramidase gene, the entire length of the desired ceramidase gene can be obtained by digesting genomic DNA with other restriction enzymes using a part of the fragment as a probe; and performing the hybridization in the same manner to obtain the deleted region. Based on the DNA fragment comprising a ceramidase gene thus obtained, the structure of the ceramidase gene and the entire amino acid sequence of ceramidase are determined.

In addition to the hybridization methods described above, PCR method may be employed to obtain a ceramidase gene of the present invention. For example, PCR method using a primer designed based on the N-terminal amino acid sequence or an internal partial amino acid sequence of ceramidase or PCR method using a cassette DNA and a cassette primer in addition to such a primer may be employed to obtain a ceramidase gene.

Next, ceramidase derived from *Pseudomonas aeruginosa* AN-17 is taken as an example and concretely described below. The above ceramidase is alkaline ceramidase of which optimum pH is in the range of pH 8.0 to 9.0.

First, a partial amino acid sequence of ceramidase produced by *Pseudomonas aeruginosa* AN-17 is examined. The N-terminal amino acid sequence of the above ceramidase has a large number in the kinds of the corresponding codons, and the number of the combinations of the primer sequences becomes extremely large. In addition, when PCR is performed using the above primer, a large number of the non-specific amplified products are formed, and among these products it is impossible to identify a product derived from a desired gene. The present inventors have performed peptide mapping using a proteolytic enzyme or a reagent for limited proteolysis typically exemplified by cyanogen bromide in order to obtain a sequence having a less corresponding codon degeneracy as an amino acid sequence to be used to design a primer, and then tried to design a primer. However, as described in Examples given below, PCR is tried in combination of 4 kinds of primers, but no specific amplified products could be obtained thereby. Accordingly, the present inventors have further respectively synthesized, based on the amino acid sequence obtained, synthetic oligonucleotide primers, i.e., an oligonucleotide primer C-89-1 (SEQ ID NO: 13) designed from a partial amino acid sequence C-89 (SEQ ID NO: 3) of the ceramidase and an oligonucleotide primer C-91-cl (SEQ ID NO: 14) designed from a partial amino acid sequence C-91 (SEQ ID NO: 4). PCR is carried out using the above 2 kinds of primers together with genomic DNA of *Pseudomonas aeruginosa* strain AN-17 as a template, whereby obtaining a specifically amplified DNA fragment. By examining the nucleotide sequence of this fragment and comparing the results with the partial amino acid sequence of the ceramidase other than those described above, it is found that the fragment contains a part of a gene encoding the ceramidase.

This amplified DNA fragment is used as a probe to perform hybridization or the like, whereby cloning a gene encoding the entire length of the ceramidase.

The entire nucleotide sequence of a gene encoding ceramidase derived from *Pseudomonas aeruginosa* strain AN-17 thus obtained above is as shown in SEQ ID NO: 16 in Sequence Listing. In addition, the amino acid sequence of the ceramidase deduced from the above nucleotide sequence is as shown in SEQ ID NO: 15 in Sequence Listing. Further, by comparing this amino acid sequence with the N-terminal amino acid sequence of the ceramidase derived from *Pseudomonas aeruginosa* strain AN-17 as shown in SEQ ID NO: 8 in Sequence Listing, it is found that the ceramidase produced by this strain can be converted after translation to a mature enzyme in which a polypeptide consisting of N-terminal 24 amino acids is deleted. This mature ceramidase has an amino acid sequence as shown in SEQ ID NO: 1 in Sequence Listing, and the nucleotide sequence of the mature ceramidase-encoding region in the nucleotide sequence of the ceramidase gene described above is as shown in SEQ ID NO: 2 in Sequence Listing, respectively. Since the amino acid sequence of the above ceramidase derived from *Pseudomonas aeruginosa* strain AN-17 and the nucleotide sequence encoding it show no homology with amino acid sequences and nucleotide sequences of known acidic ceramidases, it is suggested that this enzyme derived from *Pseudomonas aeruginosa* strain AN-17 is ceramidase belonging to a member of a novel family.

By using an entire or a part of a ceramidase gene of which an entire nucleotide sequence as described above is identified as a probe for hybridization, a DNA having a high homology with a ceramidase gene can be screened from genomic DNA libraries or cDNA libraries obtained from the organisms other than *Pseudomonas aeruginosa* strain AN-17. The hybridization may be performed under generally employed conditions. For example, a nylon membrane in which genomic DNA libraries or cDNA libraries obtained from the organisms other than the *Pseudomonas aeruginosa* strain AN-17 is immobilized is prepared. The nylon membrane is blocked at 65° C. in a pre-hybridization solution containing 6×SSC, 0.5% SDS, 5×Denhardt's reagent, 100 mg/ml herring sperm DNA, and then incubated at 65° C. overnight with adding the above probe which is $^{32}$P-labeled. This nylon membrane is firstly washed in 6×SSC at room temperature for 10 minutes; subsequently in 2×SSC containing 0.1% SDS at room temperature for 10 minutes; and further in 0.2×SSC containing 0.1% SDS at 45° C. for 30 minutes. Thereafter, an autoradiogram is prepared therefrom to detect DNA hybridizing with the probe. Incidentally, genes having various homologies can be obtained by altering conditions, such as washing.

On the other hand, a PCR primer can be designed also based on the nucleotide sequence of the ceramidase gene of the present invention. By carrying out PCR using this primer, it is possible to detect a gene fragment having a high homology with the gene of the present invention, or to obtain such a gene entirely, and also to detect an organism which produces ceramidase.

In order to confirm whether or not a gene obtained by hybridization or PCR described above is a gene which encodes a polypeptide having ceramidase activity, deduction can be made by comparing the nucleotide sequence of the gene obtained with the nucleotide sequence or the amino acid sequence of the ceramidase gene of the present invention. Alternatively, it is possible to confirm whether or not the obtained gene is a desired gene by preparing a polypeptide encoded by the gene obtained followed by assaying the ceramidase activity by means of using a method as described below.

(3) Transformant Harbouring Ceramidase Gene

The transformant of the present invention is a transformant harbouring the above ceramidase genes.

The gene of the present invention can be expressed in various hosts by ligating the gene to known vectors, and the like. Incidentally, since codon usage is different depending on a host for expressing the gene of the present invention, the expression level may be suppressed in the host in some cases. In this case, a codon used in the gene of the present invention may be used to change into a codon depending on the host used. In addition, the above expression vector is not limited only to a plasmid vector, as long as the vector does not hinder from achieving an object of the present invention, and there can be used a phage vector, a cosmid vector and the like. From the viewpoint of easily and massively producing the polypeptide of the present invention, there are desired a vector capable of inducing and expressing a foreign gene, a vector capable of expressing as a fusion protein with a reporter gene product and the like.

The transformant of the present invention can be obtained by transforming a host with a vector carrying a ceramidase gene. As a host, there can be used microorganisms such as *Escherichia coli*; animal cells; and plant cells and the like. Subsequently, a polypeptide having ceramidase activity is produced by culturing the transformant under the conditions which are usually employed.

The transformant harbouring the ceramidase gene derived from the above *Pseudomonas aeruginosa* AN-17 is named and identified as *Escherichia coli* JM109/pTCDS7, and deposited with the National Institute of Bioscience and Human-Technology, Agency of Industrial Science and Technology, Ministry of International Trade and Industry [Address: 1-3, Higashi 1-chome, Tsukuba-shi, Ibaraki-ken Japan (postal code 305-8566)] since Aug. 4, 1998 (original deposition date) [accession number: FERM BP-6728.]

Confirmation of the ceramidase expression can be carried out by determining ceramidase activity. The determination of the ceramidase activity can be carried out by using cell extracts of the transformant as a sample according to a method described in, for example, *Journal of Biological Chemistry*, 273, 14368–14373 (1998). In addition, there can be used an antibody against ceramidase, and in the case where ceramidase is expressed as a fusion with another kind of a polypeptide, an antibody against the polypeptide region may be used. When the antibody is used, the ceramidase can be detected, for instance, by subjecting cell extracts of the transformant to SDS-polyacrylamide gel electrophoresis, transferring to polyvinylidene fluoride (PVDF) membrane, and detecting with an antibody the corresponding ceramidase on the above membrane.

(4) Method for Producing Polypeptide Having Ceramidase Activity

As one big feature, the method for producing a polypeptide having ceramidase activity of the present invention comprises culturing the transformant described above, and collecting a polypeptide having ceramidase activity from the resulting culture.

In the method of the present invention, in the case where the transformant is a microorganism or a cultured cell, optimum conditions for expression of ceramidase in terms of the medium composition, the pH of a medium, the culture temperature, the culture time, the amount of an inducer used and the time period of use may be set, whereby producing the ceramidase efficiently.

The purification of ceramidase from the culture of the transformant may be carried out by a usual method. When the transformant accumulates ceramidase in the cells as in the case of *Escherichia coli*, the transformant cells are harvested by centrifugation after termination of culture. The harvested cells are disrupted by ultrasonic treatment or the like, and thereafter centrifuged to obtain a cell-free extract. This cell-free extract is used as a starting material to perform a generally employed protein purification method such as salting out as well as various chromatographies such as ion exchange, gel filtration, hydrophobic and affinity chromatographies. In some transformants used herein, an expression product is extracellularly secreted, and in such a case, the product can be purified similarly from the culture supernatant.

When the ceramidase produced by a transformant is produced in the cells, various intracellular enzymes and proteins also coexist, but only in very small amounts as compared to the ceramidase expressed, thereby making the purification extremely simple. In addition, when a vector of an extracellular secretory type is used as a vector, ceramidase is extracellularly secreted, and a ceramidase-containing fraction also coexists with medium components, and the like. Nevertheless, since the fraction usually does not substantially contain protein components which adversely affect the ceramidase purification, a complicated isolation and purification procedure which has been required for the purification of, for instance, ceramidase from the culture of *Pseudomonas aeruginosa* AN-17 strain, is not necessitated.

In addition, when *Escherichia coli* is used as a host, an expressed product may be developed as an insoluble inclusion body. In this case, the cells are harvested by centrifugation after termination of the culture, and the harvested cells are disrupted by, for example, ultrasonic treatment. Thereafter, the resulting disrupted cells are centrifuged to collect an insoluble fraction comprising the inclusion body. The inclusion body is washed and then solubilized with a usually used solubilizer for protein, such as urea or guanidine hydrochloride, and if necessary, the solubilized inclusion body is purified by carrying out various chromatographies such as ion exchange, gel filtration, hydrophobic and affinity chromatographies, and then further subjected to a re-folding procedure by dialysis procedure or dilution procedure, whereby obtaining a preparation comprising a polypeptide maintaining ceramidase activity. If necessary, the preparation thus obtained can be further purified by various chromatographies to obtain a high-purity polypeptide having ceramidase activity.

(5) Oligonucleotide Probe or Primer

The oligonucleotide probe or the primer of the present invention is not particularly limited, as long as it is capable of hybridizing under stringent conditions with the ceramidase gene described above or a gene having a nucleotide sequence complementary therewith.

The term "stringent conditions" is not particularly limited, referring to conditions, for instance, where a gene is incubated at 65° C. overnight in a solution containing 6×SSC, 0.5% SDS, 5×Denhardt's reagent, and 100 mg/ml herring sperm DNA.

The oligonucleotide probe described above can be prepared by chemically synthesizing, for instance, with a usual method according to a design based on the nucleotide sequence for the ceramidase gene of the present invention.

The length of the oligonucleotide probe described above is not particularly limited, and the probe preferably consists of 15 bases or longer, from the viewpoint of preventing a non-specific hybridization, and more preferably 18 bases or longer.

Also, the primer of the present invention includes a nucleic acid having the nucleotide sequence similar to that of the oligonucleotide probe described above. For example, the primer can be prepared by chemically synthesizing according to a design based on the nucleotide sequence for the gene of the present invention. The length of the primer is not particularly limited, and the primer can consist of 15 to 40 bases, preferably 17 to 30 bases. The primer described above can be subjected to various gene amplification methods such as polymerase chain reaction (PCR) method, whereby detecting the ceramidase gene of the present invention.

In addition, as the oligonucleotide probe or the primer described above, there can be employed a nucleic acid resulting from fragmentating a nucleic acid encoding naturally-occurring ceramidase by means of an enzymatic treatment such as a restriction enzyme treatment or an exonuclease treatment, or a physical treatment such as an ultrasonic treatment; and subjecting the fragment thus obtained to isolation and purification process by various methods for separating a nucleic acid as exemplified by agarose gel electrophoresis. The nucleic acid thus obtained as described above is desirably derived from a region having a sequence peculiar to ceramidase.

The oligonucleotide probe or the primer described above can be labeled with an appropriate label by a known method, and used to detect the ceramidase gene of the present invention. The label is not particularly limited, including, in addition to radioisotopes, fluorescent substances and ligands such as biotin and digoxigenin.

(6) Method for Detecting Gene

One big feature of the method for detecting the gene of the present invention resides in the detection of a gene in a sample to be detected by using the oligonucleotide probe and/or the primer described above.

In the detection method of the present invention, the detection of a gene may be carried out by hybridization method, or the like with the oligonucleotide probe described above, or alternatively, the detection of a gene may be carried out by means of a DNA amplification method such as PCR method using the primer described above.

When the oligonucleotide is used, a sample to be detected may, for example, be samples of a microorganism colony or a tissue segment, DNA or RNA in these samples immobilized on a membrane, and DNA or RNA extracted from these samples. Among these samples, the DNA immobilized on a membrane or the DNA extracted is preferred from the viewpoint of the stability of the samples.

When the oligonucleotide is used, a gene can be detected by a known hybridization method such as those described in *Molecular Cloning: A Laboratory Manual,* 2nd Ed. and the like.

The conditions of hybridization described above can appropriately be selected depending on the factors such as the Tm value of the probe used and the CG content of a target DNA. For example, conditions described in *Molecular Cloning: A Laboratory Manual,* 2nd Ed. can be applied.

When the primer is used, the sample to be detected may, for example, be microorganism samples such as a culture medium of a microorganism, a colony of a microorganism, and microorganism cells as well as a body sample such as skin, tissues and tissue segments.

The sample to be detected when using the primer described above may be a microorganism isolated per se, or it may be one in which the isolated microorganism is further subjected to an appropriate treatment. A solid sample such as tissues may be used in a form of an extract or a suspension. In addition, supernatant of such samples, or one obtained by further subjecting the sample to cell lysis treatment employing, for example, surfactant treatment as well as supernatant thereof may also be used. Unless the nucleic acid to be detected is affected adversely, any operation for removing other components in the sample may also be carried out.

When the detection is carried out by PCR method with the primer described above, PCR conditions can appropriately be selected depending on the factors such as the Tm value of the primer used and the length of the amplified region to be detected.

When the primer described above is used, the detection can be carried out by amplifying with DNA amplification method such as PCR method; and confirming the presence or absence of a PCR-amplified product. The method for confirming the presence or absence of amplification is not particularly limited. For example, the amplification can be confirmed by subjecting a reaction mixture of nucleic acid amplification to agarose gel electrophoresis; thereafter, staining the gel with an appropriate nucleic acid staining reagent such as ethidium bromide, SYBER Green I or the like; and detecting the presence or absence of the bands resulting from irradiation with ultraviolet rays. The bands may be detected by visual observation, or they may be detected by using, for example, a fluorescent image analyzer, or the like.

In the detection method of the present invention, the probe and the primer described above may be used in combination for the purpose of increasing the detection sensitivity. For example, the primer described above is used to amplify a ceramidase gene present in a very small amount in a sample by means of PCR method, and then a probe is used to hybridize with the gene, whereby achieving highly sensitive and accurate detection.

When a ceramidase gene is detected by the detection method of the present invention and the expression level of the gene is further determined, there can be quantified the intensity of a signal ascribed to a hybridized probe or a fluorescence intensity of a band ascribed to a product amplified using a primer, or the like.

(7) Kit for Detecting Gene of the Present Invention

One of the feature of the kit for the detection of the gene of the present invention resides in that the kit comprises the oligonucleotide probe and/or the probe described above.

The kit of the present invention may further comprise various reagents for hybridization typically exemplified by a membrane for immobilizing a nucleic acid and hybridization buffer; PCR reagents such as thermostable DNA polymerase, dNTPs mixture and PCR buffer; reagents for detecting a probe or an amplified DNA; a medium for microbial growth; and a reagent for extracting a nucleic acid from a sample.

(8) Antibody or Fragment Thereof, Which is Capable of Specifically Binding to Polypeptide Having Ceramidase Activity The antibody or a fragment thereof, which is capable of specifically binding to the polypeptide of the present invention is not particularly limited, as long as it is capable of specifically binding to the polypeptide, and may be either of a polyclonal antibody or a monoclonal antibody. Further, there can be employed an antibody modified by a known method or a derivative of an antibody, including, for example, a humanized antibody, a Fab fragment, a single chain antibody and the like. Furthermore, the antibody of the present invention can readily be obtained by immunizing a rabbit or a mouse using an entire or a part of the polypeptide of the present invention, for example, by a method described in *Current Protocols in Immunology* [Ed. by John E. Coligan, Issued by John Wiley & Sons, Inc. (1992)]. The antibody can also be produced by means of a gene engineering technique. In addition, the antibody or a fragment thereof, which is capable of specifically binding to a certain partial fragment of a polypeptide can also be encompassed.

Further, a fragment of the antibody is obtained by purifying the antibody thus obtained, and then treating with a peptidase or the like. The antibody or a fragment thereof thus obtained may be applied to detection of a ceramidase-producing microorganism, affinity chromatography, screening of various libraries (genomic DNAs or cDNAs), a pharmaceutical, a diagnostic agent, a reagent for research and development, and the like.

Moreover, the antibody or the fragment thereof of the present invention may also be modified in various ways for the purpose of facilitating a detection by enzyme immunoassay, fluorescent immunoassay, luminescent immunoassay, and the like.

(9) Method for Detecting Polypeptide

One big feature of the method for detecting the polypeptide of the present invention resides in the detection of a polypeptide having ceramidase activity by using the antibody or the fragment thereof described above.

In the present invention, a sample to be detected includes, for instance, protein samples such as disrupted microbial cells, an extract or a product obtained by washing tissues such as skin, and a membrane onto which a protein derived from tissues or microorganisms is immobilized.

The detection of a specific binding of the antibody or the fragment thereof to the polypeptide described above may be carried out by a known method, such as enzyme immunoassay, fluorescent immunoassay, luminescent immunoassay and the like.

(10) Kit for Method for Detecting Polypeptide of the Present Invention

One feature of the kit for the method for detecting a polypeptide of the present invention resides in that the kit comprises the antibody or the fragment thereof described above.

The kit of the present invention may further comprise reaction buffer, a labeled secondary antibody, a chromogenic reagent, and the like.

(11) Method for Detecting Atopic Dermatitis

As described above, the microorganism which produces ceramidase is considered to be causative of or to be involved in exacerbation of atopic dermatitis.

According to the method for detecting atopic dermatitis of the present invention, atopic dermatitis can be detected by detecting in a sample from skin a polypeptide having ceramidase activity, or a gene encoding such a polypeptide.

The sample derived from skin used in the method for detecting atopic dermatitis of the present invention is not particularly limited, and may be a scale of skin of an individual to be tested, a smear of skin obtained by wiping the skin with a cotton swab or a gauze, a product obtained by washing skin, and the like. The method for collecting such samples is not particularly limited. Examples thereof include a method of collecting a scale directly from skin of an individual to be tested; a method of wiping skin of an individual to be tested with a cotton swab or a gauze; or a method of collecting a washing product comprising bringing a cylinder of a suitable size into close contact with skin of an individual to be tested, the cylinder being filled with suitable fluid for washing such as physiological saline or phosphate buffer, and then washing the skin with the fluid for washing.

These samples thus obtained may directly be used for detection of the polypeptide described above or for detection of the gene encoding such a polypeptide. Further, the culture resulting from culturing a microorganism contained in the sample may be cultured in an appropriate medium, and used as a sample to be detected, whereby improving the detection sensitivity. The medium used for culturing the microorganism is not particularly limited, as long as the microorganism in the sample from skin can be grown, and the medium can efficiently produce ceramidase. For example, a medium containing, as carbon sources and/or nitrogen sources, glycerol, glucose, sucrose, syrups, yeast extracts, peptone, corn steep liquor, meat extracts, delipidated soybean, ammonium sulfate, ammonium nitrate, and the like, is appropriately used. In addition to those listed above, minerals and metal salts such as sodium salts, potassium salts, magnesium salts, zinc salts, phosphates, and the like may also be contained. In addition, to the medium there may also be added 0.001 to 1% of a lipid such as sphingomyelin and ceramides, or a surfactant such as taurodeoxycholates, in order to increase the expression level of the ceramidase, whereby improving the detection sensitivity. The culture conditions for the microorganisms are not particularly limited, it is preferable that the microorganism is cultured at 25° to 37° C. for 1 to 7 days. After termination of the culture, the culture may directly be used for a detection procedure, or alternatively, when a polypeptide is detected, a culture supernatant obtained by centrifuging the culture may be used as a sample.

The method for detecting atopic dermatitis of the present invention can be carried out by detecting a gene encoding a polypeptide having ceramidase activity using the oligonucleotide probe or the primer described above, or the method may also be carried out by detecting a polypeptide having ceramidase activity using the antibody or the fragment thereof described above, which is capable of specifically binding to the polypeptide having ceramidase activity. In addition, for the purpose of simply detecting atopic dermatitis, there may be employed a kit for detecting the gene encoding a polypeptide having ceramidase activity described above, or a kit for detecting the polypeptide having ceramidase activity described above. The kits described above may further comprise a tool for obtaining a sample described below, including, for example, a kit further comprising a cotton swab and a culture medium.

In the method for detecting atopic dermatitis of the present invention, when the gene encoding a polypeptide having ceramidase activity is detected by using an oligonucleotide probe, for example, a nucleic acid prepared by a known method from a sample from skin of an individual to be tested is hybridized with an oligonucleotide probe designed based on a nucleotide sequence of the ceramidase gene under appropriate hybridization conditions for detecting the formed hybrid. For example, the gene encoding a polypeptide having ceramidase activity can be detected by dot blot hybridization where a nucleic acid prepared from a sample from skin is immobilized on a nitrocellulose membrane or the like. Alternatively, a sample is immobilized directly on a nitrocellulose membrane, and the nucleic acid contained in the sample is exposed by appropriate lysis treatment, and then hybridized, whereby the formed hybrid can be detected.

In the method for detecting atopic dermatitis of the present invention, when the gene encoding a polypeptide having ceramidase activity is detected by a means of gene amplification, a reaction mixture is prepared from a sample from skin of an individual to be tested or a nucleic acid prepared from such sample and a primer designed based on the nucleotide sequence of a ceramidase gene, and the reaction mixture is subjected to gene amplification reaction. When PCR method is employed as gene amplification reaction, the procedures described in Section (6) above are performed to amplify a DNA, and an amplified DNA is then detected. For example, a reaction mixture is prepared by adding a pair of primers prepared based on a nucleotide sequence of a ceramidase gene and a sample from skin, together with DNA polymerase and dNTPs, and amplification reaction is performed under conditions appropriate for the primer sequence and the length of the region expected to be amplified. After termination of the reaction, the reaction mixture is analyzed by agarose gel electrophoresis or the like to examine the presence or absence of an amplification of the DNA fragment derived from a desired gene.

When a gene encoding a polypeptide having ceramidase activity is detected in a sample from skin by means of the method described above, the site of skin where the sample is collected is diagnosed to have atopic dermatitis.

In the method for detecting atopic dermatitis of the present invention, when the polypeptide having ceramidase activity is detected, an antibody or a fragment thereof, which is capable of specifically binding to the polypeptide having ceramidase activity is used to examine whether or not a polypeptide bound to the antibody or the fragment thereof described above is present in the sample from skin of an individual to be tested. The detection of such a polypeptide can be performed by known immunological experimental procedures such as immunodiffusion, latex agglutination method and enzyme immunoassay. From the aspects of the detection sensitivity and the simplicity of the operation, the enzyme immunoassay is the most practical method.

When the polypeptide having ceramidase activity is detected in a sample from skin by the method described above, the site of skin where the sample is obtained is diagnosed to have atopic dermatitis.

(12) Kit for Detecting Atopic Dermatitis

In order to more simply perform the detection of atopic dermatitis described above, the kit for detecting the gene encoding a polypeptide having ceramidase activity described above or the kit for detecting the polypeptide having ceramidase activity described above may further comprise a tool for collecting a sample such as a cotton swab and a culture medium.

According to the present invention, there are provided for the first time an amino acid sequence of alkaline ceramidase as well as a nucleotide sequence encoding it, whereby providing gene engineering method for producing a polypeptide having ceramidase activity using the above gene, a method for detecting the ceramidase, and also a method for detecting atopic dermatitis. In the method for producing ceramidase of the present invention, since there is no need to add a sphingolipid to a medium for inducing an expression of ceramidase and there is no contamination of, for example, enzymes capable of simultaneously inducing, the enzymes including sphingomyelinase, or there is no admixture of sphingolipid added to the medium or its degradation products, the desired ceramidase can readily be purified. Also, there are provided a probe or a primer, which is capable of hybridizing specifically with the ceramidase gene of the present invention as well as an antibody or a fragment thereof, which is capable of specifically binding to the polypeptide having ceramidase activity of the present invention. By using the above probe, primer, and antibody or fragment thereof, ceramidase can be detected simply and at a high sensitivity. In addition, by using the above probe, primer, and antibody or fragment thereof, there is exhibited an excellent effect that the atopic dermatitis can be simply detected.

EXAMPLES

The present invention is concretely illustrated by means of the following examples, without intending to restrict the scope of the present invention thereto.

Example 1

Cloning of Structural Gene of Ceramidase (1) Extraction and Purification of Genomic DNA A ceramidase-producing microorganism *Pseudomonas aeruginosa* strain AN-17 (FERM P-15699) was inoculated to 200 ml of a PY medium (0.5% polypeptone, 0.1% yeast extract, 0.5% sodium chloride, pH 7.2) and cultured at 25° C. for 23 hours. After termination of the culture, a culture medium obtained was centrifuged to harvest cells. The harvested cells were suspended in 10 ml of TE buffer (10 mM Tris-HCl, 1 mM EDTA, pH 8.0), and then thereto was added 0.2 ml of a 50 mg/ml albumin lysozyme solution, and reacted at 30° C. for 15 minutes. Subsequently, to the solution obtained after termination of the reaction was added 2 ml of 10% SDS, and the mixture was stirred gently. Immediately after the solution became viscous, 10 ml of TE buffer-saturated phenol and 1.5 ml of 5M NaCl were added to the solution, and stirred gently at room temperature for 1 hour. The solution obtained after stirring was centrifuged at 2500 rpm for 10 minutes, and supernatant was collected. To the solution thus obtained was added an equivolume of chloroform and stirred for 10 minutes, and then centrifuged at 1500 rpm for 10 minutes to collect supernatant. To the supernatant obtained above was added once again an equivolume of chloroform, stirred, and centrifuged to collect supernatant (hereinafter a series of these operations is referred to as phenol-chloroform treatment). To the supernatant thus collected, an equivolume of isopropanol was added slowly, and a DNA precipitating on an interface was collected by winding around a pasteur pipette, and then dissolved in 10 ml of a TE buffer. To the solution thus obtained was added 20 $\mu$l of RNase A (those prepared by dissolving RNase in 10 mM Tris-HCl, pH 7.5, 15 mM NaCl so as to have a concentration of 10 mg/ml, and then heat-treating at 100° C. for 15 minutes), and the mixture was incubated at 50° C. for 1 hour. To the solution after incubation, 10 $\mu$l of a 20 mg/ml protease K solution, 200 $\mu$l of 5M NaCl, and 400 $\mu$l of 10% SDS were further added, and the mixture was incubated at 37° C. for 1 hour, whereby a reaction is performed. The solution after the reaction was allowed to cool to room temperature, and subjected to phenol-chloroform treatment. The treatment was repeated twice, and to an aqueous phase obtained was added an equivolume of isopropanol and a 1/10 volume of 3M sodium acetate. The mixture was cooled at −20° C. for 1 hour, and then centrifuged at 10,000 rpm for 10 minutes to obtain sedimentation. The obtained sediment was rinsed with 70% ethanol, and dissolved in TE buffer to obtain genomic DNA solution. By the above procedures, 1.1 mg of genomic DNA was obtained.

(2) Determination of Partial Amino Acid Sequence of Ceramidase

Ceramidase produced by *Pseudomonas aeruginosa* strain AN-17 (FERM P-15699) was purified according to a method described in *Journal of Biological Chemistry*, 273, No.23, 14368–14373 (1998). About 5 $\mu$g of the ceramidase obtained was applied to SDS-polyacrylamide gel electrophoresis to be electrophoresed. Subsequently, the proteins on the gel were transferred to a PVDF membrane ("Immobilon-P," manufactured by Millipore) by means of electroblotting. A region corresponding to a band of ceramidase on this membrane (about 50 pmol) was cut out, and enzyme-digested at 37° C. for 16 hours with shaking in 100 $\mu$l of a 20 mM Tris-HCl buffer containing 0.2 mg of lysyl endopeptidase (0.9 U) and 8% acetonitrile. This enzyme-digested solution was applied to reverse phase chromatography to purify a peptide fragment. The peptide fragment thus obtained was analyzed by Edman degradation using gas phase peptide sequencer Model 477 (manufactured by Applied Biosystem) to determine the ceramidase internal partial amino acid sequences C-89 (SEQ ID NO: 3 in Sequence Listing), C-91 (SEQ ID NO: 4 in Sequence Listing), S-90 (SEQ ID NO: 5 in Sequence Listing), C-86 (SEQ ID NO: 6 in Sequence Listing) and C-121 (SEQ ID NO: 7 in Sequence Listing).

On the other hand, apart from the above, the PVDF membrane described above was applied to a peptide sequencer without a treatment with lysyl endopeptidase to determine an N-terminal amino acid sequence N-Term (SEQ ID NO: 8 in Sequence Listing).

(3) Amplification by PCR of Ceramidase Gene-Containing DNA Fragment

Based on the N-terminal amino acid sequence and the internal partial amino acid sequence determined in Example 1-(2), each primer as shown in each of SEQ ID NOS: 9 to 11 in Sequence Listing was designed and synthesized by a DNA synthesizer.

Specifically, a sense mix primer S90-1 as shown in SEQ ID NO: 9 and a sense mix primer S90-2 as shown in SEQ ID NO: 10, each corresponding to S-90 as shown in SEQ ID NO: 5; an anti-sense mix primer C89-cl as shown in SEQ ID NO: 11, an anti-sense mix primer C89-c2 as shown in SEQ ID NO: 12 and an anti-sense mix primer C89-1 as shown in SEQ ID NO: 13, each corresponding to C-89 as shown in SEQ ID NO: 3; and an anti-sense mix primer C91-cl as shown in SEQ ID NO: 14 corresponding to C-91 as shown in SEQ ID NO: 4 were respectively synthesized.

Each of these primers was subjected to PCR reaction. The PCR was performed by using Gene Amp Reagent Kit (manufactured by Perkin Elmer). Forty-reaction cycles of the reaction were carried out, wherein 1 cycle consists of at 94° C. for 0.5 minutes, at 51° C. for 0.5 minutes, and at 72° C. 1 minute.

In a PCR reaction with the combination of primer C89-1 with primer C91-cl using the genomic DNA obtained in Example 1-(1) as a template, amplification of a specific band corresponding to about 350 bp was detected. None of the combinations of S90-1 with C89-cl, S90-1 with C89-c2, S90-2 with C89-cl, and S90-2 with C89-c2 showed any amplification of specific bands.

The amplified DNA fragment of about 350 bp obtained above was collected from a gel after the agarose gel electrophoresis, and the collected DNA fragment was ligated to pGEM-T easy vector (manufactured by Promega) to prepare a recombinant plasmid. Using this plasmid as a template, the nucleotide sequence of the amplified DNA fragment obtained above was determined by dideoxy method. As a result, the nucleotide sequence obtained was found to have a nucleotide sequence which encoded each of the partial amino acid sequences of the ceramidase, namely, C-89, C-86, C-121 and C-91, whereby clarifying that this amplified DNA fragment was a part of the gene encoding a desired ceramidase.

(4) Detection of Ceramidase Gene-Containing DNA Fragment

The PCR amplified DNA fragment obtained in Example 1-(3) was used as a probe to screen a genomic DNA fragment comprising a ceramidase gene.

First, 5 μg of the genomic DNA prepared in Example 1-(1) was digested with 100 U of each of the restriction enzymes SphI, ApaI, KpnI, XhoI, SalI, HincII, HindIII, EcoRV, EcoRI, PstI, SmaI, BamHI, NotI and SacII at 37° C. for 22 hours, and the resulting restriction enzyme-digested DNA was applied to 1% agarose gel electrophoresis. After the electrophoresis, the DNA was transferred to a nylon membrane [Hybond-N+, manufactured by Amersham] by means of Southern blotting. As a hybridization probe, one obtained by labeling 0.1 μg of the PCR-amplified DNA fragment obtained in Example 1-(3) with $^{32}$P using DNA labeling kit (ReadyTo Go, manufactured by Pharmacia) according to the protocol of the kit was employed.

The nylon membrane described above was pre-hybridized at 65° C. for 1 hour or longer in a hybridization solution containing 0.5M Church-Method phosphate buffer [*Proc. Natl. Acad. Sci. U.S.A.*, 81, 1991–1995 (1984)], pH 7.0, 7% SDS and 1 mM EDTA, and then the labeled probe described above was added thereto so as to have a concentration of 6 fmol/ml, and the hybridization was carried out at 65° C. overnight. Subsequently, the nylon membrane was washed three times each at 65° C. for 15 minutes with a washing solution previously warmed to 65° C. (composition: 1% SDS, 40 mM sodium phosphate buffer). After removal of excessive water from the nylon membrane, the nylon membrane was brought into contact with imaging plate (manufactured by Fuji Photo Film Co., Ltd.) for 20 minutes to be photosensitized. After the photosensitization, imaging plate was analyzed by BAS 1000 Imaging Analyzer (manufactured by Fuji Photo Film Co., Ltd.) to detect a probe on the nylon membrane. As a result, the digested products by SphI, ApaI, KpnI, XhoI, SalI, HincII, HindIII, EcoRV, EcoRI, PstI, SmaI, BamHI, NotI and SacII were found to have the signals ascribed to the probes hybridized at the sites of approximately 7.1 kb, 2.8 kb, 12.6 kb, 5.8 kb, 1.8 kb, 1.8 kb, 13.7 kb, 12.6 kb, 9 kb, 6 kb, 3.5 kb, 6.7 kb, 11.8 kb and 1.5 kb, respectively.

(5) Ceramidase Gene Cloning

Based on the results of Example 1-(4), an about 2.8 kb ApaI fragment was cloned. Ten milligrams of ApaI-digested genomic DNA was separated by 1% agarose gel electrophoresis, and an agarose gel at the position corresponding to a size of about 2.8 kb was cut out. Using Sephaglas BandPrep Kit (manufactured by Amersham Pharmacia), a DNA fragment was extracted from the gel and purified, and this DNA fragment was inserted into pBluescript II SK (manufactured by Toyobo Co., Ltd.) at ApaI site to prepare a recombinant plasmid. *Escherichia coli* strain JM109 was transformed with this plasmid, and cultured overnight on L plate of an agar medium (composition: 1% tryptone, 0.5% yeast extract, 1% NaCl, pH 7.2) containing 100 μg/ml of ampicillin, and from the colonies formed 300 colonies were selected and inoculated onto a nylon membrane (Hybond-N, manufactured by Amersham) placed on the same agar plate. After culturing at 37° C. for 16 hours, the nylon membrane was treated for 5 minutes on a filter paper immersed in an alkaline denaturation solution (composition: 0.5M NaOH, 1.5M NaCl) (denaturation), and for 5 minutes on a filter paper immersed in a neutralization solution [composition: 0.5M Tris-HCl (pH 7.5), 3M NaCl] (neutralization), and then rinsed with 2×SSC (composition of 1×SSC: 0.15M NaCl, 0.015M sodium citrate, pH 7.0).

This nylon membrane was hybridized under the conditions described above using as a probe the PCR-amplified DNA fragment obtained in Example 1-(3), and 2 colonies exhibited the signals. One of these colonies was used to prepare a plasmid, which was named pSCA59 and used to determine the nucleotide sequence of the inserted DNA fragment in this plasmid. As a result, the nucleotide sequences corresponding to the amino acid sequence obtained in Example 1-(2), C-89, C-86, C-121 and C-91 were found together with the stop codons in the same frames, while no nucleotide sequence corresponding to an N-terminal amino acid sequence N-Term or S-90 was found. In other words, it was clarified that this plasmid contained 3' terminal (C-terminal region) containing a stop codon of a ceramidase gene, but not 5' terminal (N-terminal region).

Subsequently, in order to obtain the entire length of a ceramidase gene, a DNA fragment encoding the region near the N-terminal which was deleted in pSCA59 was screened by Southern hybridization method in the same manner as described above. The probe used herein was a KpnI/SacII-digested fragment of pSCA59 having a size of about 560 bp which contained the sequence near the 5' terminal of the ceramidase gene. A KpnI/SacII fragment in a size of about 560 bp isolated by agarose gel electrophoresis was labeled with $^{32}$P in the same manner as described above, and subjected to Southern hybridization in the same manner as described above. As a result, each of the probes was hybridized with an SphI-digested fragment at a site of about 7.1 kb, with an ApaI-digested fragment at a site of about 2.8 kb, with an XhoI-digested fragment at a site of about 5.8 kb, with an EcoRI-digested fragment at a site of about 9 kb, with a PstI-digested fragment at a site of about 6 kb, with an SmaI-digested fragment at a site of about 3.5 kb, with a BamHI-digested fragment at a site of about 2.1 kb, and with an SacII-digested fragment at a site of about 2.5 kb, respectively.

Based on the above results, an about 2.1 kb BamHI fragment was cloned. Ten milligrams of a BamHI-digested genomic DNA was separated by 1% agarose gel electrophoresis, and an agarose gel was cut out at the position corresponding to a size of about 2.1 kb, and a DNA fragment extracted and purified from the gel using Sephaglas BandPrep Kit was inserted into pGEM-3Zf(+) (manufactured by Promega) at a BamHI site. Nine positive colonies were obtained by transforming *Escherichia coli* strain JM109 with this plasmid, and performing colony hybridization in the same manner as described above. A plasmid was prepared from one of these colonies, and named pGCB38. Thereafter, the nucleotide sequence of the inserted DNA fragment in the above pGCB38 was determined. First, various deletion mutants were prepared by digesting this plasmid with restriction enzymes PstI and XbaI, and then treating with Exonuclease III (manufactured by Nippon Gene) and Mung Bean Nuclease (manufactured by Nippon Gene) according to a standard method. The nucleotide sequence of the ceramidase gene inserted in pGCB38 was determined by analyzing the nucleotide sequences of these mutants and pGCB38 with dideoxy method. As a result, the nucleotide sequences corresponding to a ceramidase N-terminal amino acid sequence N-Term and S-90 were found, whereby clarifying that pGCB38 contained the region encoding the N-terminal of the ceramidase gene.

A restriction map of the inserted DNA fragment of plasmids pSCA59 and pGCB 28 is shown in FIG. 1. Based on the results of the analysis of the nucleotide sequences of the both plasmids, the entire nucleotide sequence of the ceramidase gene and the amino acid sequence of the ceramidase were determined. The nucleotide sequence of open reading frame (ORF) encoding the ceramidase produced by *Pseudomonas aeruginosa* strain AN-17 is as shown in SEQ ID NO: 16 in Sequence Listing, and the amino acid sequence encoded by this ORF is as shown in SEQ ID NO: 15 in Sequence Listing. A nucleotide sequence encoding mature ceramidase, which was clarified by an N-terminal amino acid sequence N-Term of the ceramidase obtained in Example 1-(2) (SEQ ID NO: 8 in Sequence Listing), is shown in SEQ ID NO: 2 in Sequence Listing. The amino acid sequence of mature ceramidase encoded by this nucleotide sequence is shown in SEQ ID NO: 1 in Sequence Listing.

Example 2

Construction of Plasmid Expressing Ceramidase Polypeptide

A plasmid expressing ceramidase was constructed by following the procedures shown below.

Deletion mutants of plasmid pGCB38 prepared in Example 1-(5), pGCB38-D13, has an insertion of up to 15 bases upstream of an initiation codon of the ORF encoding ceramidase. A DNA fragment of about 1.3 kb resulting from digestion of this plasmid with restriction enzymes HindIII and BamHI was isolated and purified by 1% agarose gel electrophoresis to obtain DNA Fragment-1. On the other hand, a DNA fragment of about 1.6 kb resulting from digestion of plasmid pSCA59 with restriction enzymes HindIII and BamHI was isolated and purified by 1% agarose gel electrophoresis to obtain DNA Fragment-2. Subsequently, a HindIII-digested plasmid pTV119N (manufactured by Takara Shuzo Co., Ltd.) was ligated with a mixture of DNA Fragment-1 and DNA Fragment-2 obtained above. Thereafter, a recombinant plasmid in which the insertion fragments were properly inserted in the order of DNA Fragment-1 and DNA Fragment-2 downstream of a lac promoter of the pTV119N was selected, and named pTCD11. Further, the pTCD11 was digested with a restriction enzyme SmaI to prepare plasmid pTCDS7 in which a 500 bp SmaI fragment was deleted. The *Escherichia coli* strain JM109 transformed with this plasmid was named and indicated-as JM109/pTCDS7 under accession number FERM BP-6728 and deposited to National Institute of Bioscience and Human-Technology, Agency of Industrial Science and Technology, Ministry of International Trade and Industry.

Example 3

Expression of Ceramidase in Transformed *E. coli*

The *Escherichia coli* strain JM109/pTCDS7 obtained in Example 2 was inoculated in 5 ml of L medium containing 100 μg/ml of ampicillin, and cultured with shaking at 37° C. overnight, and a 1 ml portion of the culture medium was inoculated to 200 ml of the same L medium. After culturing at 37° C. until the turbidity (absorbance at 600 nm) reached about 0.6, to the resulting culture was added isopropyl-β-D-thiogalactoside (IPTG) so as to give a final concentration of 0.1 mM, and then further cultured with shaking at 37° C. for 8 hours. After termination of the culture, the cells were harvested by centrifugation of the culture medium, suspended in 3 ml of a 10 mM Tris-HCl buffer (pH 8.0) containing 0.5 mM 4-(2-aminoethyl)benzenesulfonyl fluoride hydrochloride, and treated ultrasonically to disrupt the cells. The disrupted cell fluid thus obtained was centrifuged to collect supernatant, which was used as a crude enzyme solution.

This crude enzyme solution was assayed for its ceramidase activity using C12-NBD-ceramide as a substrate according to the method described in *Journal of Biological Chemistry*, 273, 14368–14373 (1998). Specifically, a reaction solution was prepared by dissolving 550 pmol of C12-NBD-ceramide, 2.5 mM calcium chloride, 0.25% (w/v) Triton X-100 and an appropriate amount of the crude enzyme solution in 20 μl of a 25 mM Tris-HCl buffer (pH 8.5), and the reaction solution was incubated at 37° C. for 20 minutes. The resulting reaction mixture was incubated in a boiling water for 5 minutes to terminate the reaction, and the reaction mixture was further dried under reduced pressure. The dried product was dissolved in chloroform/methanol=2/1 (weight ratio) solution, and subjected to silica gel thin layer chromatography [eluent: chloroform/methanol/25% aqueous ammonia=90/20/0.5 (volume ratio)]. After the development, the amounts of C12-NBD-ceramide and its degradation product C12-NBD-fatty acid at the excitation wavelength of 475 nm and the fluorescence wavelength of 525 nm were assayed with a CS-9300 chromatoscanner (manufactured by Shimadzu Corporation). One unit of this enzyme was defined as an amount of enzyme required for the formation of 1 μmol of C12-NBD-fatty acid per one minute under the conditions described above. As a result, it was shown that the *Escherichia coli* strain JM109/pTCDS7 harbouring the ceramidase gene according to the present invention produced about 32 units of the ceramidase per 1 L of the culture medium.

Example 4

Detection of Atopic Dermatitis

Based on the nucleotide sequence of the ceramidase gene described above, primer 382U, a primer for upstream, and primer 884L, a primer for downstream, were designed and synthesized as primers for detecting a ceramidase gene. The nucleotide sequences of primer 382U and primer 884L are as shown in SEQ ID NOS: 17 and 18 in Sequence Listing. When a PCR was performed using these two primers and a ceramidase gene of the nucleotide sequence shown in SEQ ID NO: 2 in Sequence Listing as a template, a DNA fragment of 523 bp was amplified.

Skin-derived samples were collected from skin of each of 24 patients with atopic dermatitis and 8 normal individuals in the following procedures. Skin of an individual to be tested was wiped with a sterilized cotton swab, and the swab was immersed in 200 μl of a sterilized distilled water, and stirred vigorously prior to collecting a sample. The collected sample was heated at 100° C. for 5 minutes to obtain a sample solution to be used for a PCR.

The PCR was performed using EXTaq (manufactured by Takara Shuzo Co., Ltd.). 100 μl of a PCR reaction solution containing 5 μl of the sample solution, each. 0.2 μM of primer 382U and primer 884L, each 0.2 mM of dATP, dCTP, dGTP and dTTP, a 2.5 U of EXTaq was prepared using a reaction buffer appended to EXTaq for 40 cycles, wherein one cycle consists of 1 minute at 94° C., 1 minute at 60° C., and 1 minute at 72° C. A part of the resulting reaction mixture was subjected to an agarose gel electrophoresis, and the resulting gel after electrophoresis was stained with ethidium bromide to examine the presence or absence of an amplification of the DNA fragment.

As a result, in samples of 15 out of 24 patients with atopic dermatitis, a specific amplification of DNA fragment of about 500 bp, an index for the presence of a ceramidase gene was found. On the other hand, no such amplification of the fragment was noted in any of 8 samples derived from the normal individuals.

EQUIVALENT

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An isolated gene encoding a polypeptide having an amino acid sequence as shown in SEQ ID NO: 1.

2. The isolated gene according to claim 1, wherein the gene has a nucleotide sequence as shown in SEQ ID NO: 2.

3. An isolated gene capable of hybridizing with the gene of claim 1 under stringent conditions wherein incubation is made at 65° C. for overnight in a solution containing 6×SSC (composition of 1×SSC:0.15M NaCl, 0.015M sodium citrate, pH 7.0), 0.5% SDS, 5×Denhardt's reagent, and 100 mg/ml herring sperm DNA, and encoding a polypeptide having ceramidase activity.

4. A transformant harbouring the isolated gene of claim 1.

5. A method for producing a polypeptide having ceramidase activity, comprising culturing the transformant of claim 5, and collecting a polypeptide having ceramidase activity from the resulting culture.

6. A transformant harbouring the isolated gene of claim 3.

7. A method for producing a polypeptide having ceramidase activity, comprising culturing the transformant of claim 6, and collecting a polypeptide having ceramidase activity from the resulting culture.

* * * * *

SEQUENCE LISTING

<160> NUMBER OF SEQ ID NOS: 18

<210> SEQ ID NO 1
<211> LENGTH: 645
<212> TYPE: PRT
<213> ORGANISM: Pseudomonas aeruginosa
<220> FEATURE:
<223> OTHER INFORMATION: any n or Xaa = Unknown

<400> SEQUENCE: 1

Asp Asp Leu Pro Tyr Arg Phe Gly Leu Gly Lys Ala Asp Ile Thr Gly
 1               5                  10                  15

Glu Ala Ala Glu Val Gly Met Met Gly Tyr Ser Ser Leu Glu Gln Lys
            20                  25                  30

Thr Ala Gly Ile His Met Arg Gln Trp Ala Arg Ala Phe Val Ile Glu
        35                  40                  45

Glu Ala Ala Ser Gly Arg Arg Leu Val Tyr Val Asn Thr Asp Leu Gly
    50                  55                  60

Met Thr Phe Gln Ala Val His Leu Lys Val Leu Ala Arg Leu Lys Ala
65                  70                  75                  80

Lys Tyr Pro Gly Val Tyr Asp Glu Asn Asn Val Met Leu Ala Ala Thr
                85                  90                  95

His Thr His Ser Gly Pro Gly Gly Phe Ser His Tyr Ala Met Tyr Asn
            100                 105                 110

Leu Ser Val Leu Gly Phe Gln Glu Lys Thr Phe Asn Ala Ile Val Asp
        115                 120                 125

Gly Ile Val Arg Ser Ile Glu Arg Ala Gln Ala Arg Leu Gln Pro Gly
    130                 135                 140

Arg Leu Phe Tyr Gly Ser Gly Glu Leu Arg Asn Ala Ser Arg Asn Arg
145                 150                 155                 160

Ser Leu Leu Ser His Leu Lys Asn Pro Asp Ile Gly Tyr Glu Asp Gly
                165                 170                 175

Ile Asp Pro Gln Met Ser Val Leu Ser Phe Val Asp Ala Asn Gly Glu
            180                 185                 190

Leu Ala Gly Ala Ile Ser Trp Phe Pro Val His Ser Thr Ser Met Thr
        195                 200                 205

Asn Ala Asn His Leu Ile Ser Pro Asp Asn Lys Gly Tyr Ala Ser Tyr
    210                 215                 220

His Trp Glu His Asp Val Ser Arg Lys Ser Gly Phe Val Ala Ala Phe
225                 230                 235                 240

Ala Gln Thr Asn Ala Gly Asn Leu Ser Pro Asn Leu Asn Leu Lys Pro

-continued

```
                245                 250                 255
Gly Ser Gly Pro Phe Asp Asn Glu Phe Asp Asn Thr Arg Glu Ile Gly
            260                 265                 270
Leu Arg Gln Phe Ala Lys Ala Tyr Glu Ile Ala Gly Gln Ala Gln Glu
        275                 280                 285
Glu Val Leu Gly Glu Leu Asp Ser Arg Phe Arg Phe Val Asp Phe Thr
    290                 295                 300
Arg Leu Pro Ile Arg Pro Glu Phe Thr Asp Gly Gln Pro Arg Gln Leu
305                 310                 315                 320
Cys Thr Ala Ala Ile Gly Thr Ser Leu Ala Ala Gly Ser Thr Glu Asp
                325                 330                 335
Gly Pro Gly Pro Leu Gly Leu Glu Glu Gly Asn Asn Pro Phe Leu Ser
            340                 345                 350
Ala Leu Gly Gly Leu Leu Thr Gly Val Pro Pro Gln Glu Leu Val Gln
        355                 360                 365
Cys Gln Ala Glu Lys Thr Ile Leu Ala Asp Thr Gly Asn Lys Lys Pro
    370                 375                 380
Tyr Pro Trp Thr Pro Thr Val Leu Pro Ile Gln Met Phe Arg Ile Gly
385                 390                 395                 400
Gln Leu Glu Leu Leu Gly Ala Pro Ala Glu Phe Thr Val Met Ala Gly
                405                 410                 415
Val Arg Ile Arg Arg Ala Val Gln Ala Ala Ser Glu Ala Ala Gly Ile
            420                 425                 430
Arg His Val Val Phe Asn Gly Tyr Ala Asn Ala Tyr Ala Ser Tyr Val
        435                 440                 445
Thr Thr Arg Glu Glu Tyr Ala Ala Gln Glu Tyr Glu Gly Gly Ser Thr
    450                 455                 460
Leu Tyr Gly Pro Trp Thr Gln Ala Ala Tyr Gln Gln Leu Phe Val Asp
465                 470                 475                 480
Met Ala Val Ala Leu Arg Glu Arg Leu Pro Val Glu Thr Ser Ala Ile
                485                 490                 495
Ala Pro Asp Leu Ser Cys Cys Gln Met Asn Phe Gln Thr Gly Val Val
            500                 505                 510
Ala Asp Asp Pro Tyr Ile Gly Lys Ser Phe Gly Asp Val Leu Gln Gln
        515                 520                 525
Pro Arg Glu Ser Tyr Arg Ile Gly Asp Lys Val Thr Val Ala Phe Val
    530                 535                 540
Thr Gly His Pro Lys Asn Asp Leu Arg Thr Glu Lys Thr Phe Leu Glu
545                 550                 555                 560
Val Val Asn Ile Gly Lys Asp Gly Lys Gln Thr Pro Val Thr Val Ala
                565                 570                 575
Thr Asp Asn Asp Trp Asp Thr Gln Tyr Arg Trp Glu Arg Val Gly Ile
            580                 585                 590
Ser Ala Ser Lys Ala Thr Ile Ser Trp Ser Ile Pro Pro Gly Thr Glu
        595                 600                 605
Pro Gly His Tyr Tyr Ile Arg His Tyr Gly Asn Ala Lys Asn Phe Trp
    610                 615                 620
Thr Gln Lys Ile Ser Glu Ile Gly Gly Ser Thr Arg Ser Phe Glu Val
625                 630                 635                 640
Leu Gly Thr Thr Pro
                645
```

<210> SEQ ID NO 2

<211> LENGTH: 1941
<212> TYPE: DNA
<213> ORGANISM: Pseudomonas aeruginosa
<220> FEATURE:
<223> OTHER INFORMATION: any n or Xaa = Unknown

<400> SEQUENCE: 2

```
gacgacctgc cctaccgctt cggcctgggc aaggcggaca tcaccggcga agccgccgaa      60
gtcggcatga tgggttactc ctccctcgaa cagaagaccg ccggcatcca catgcgccag     120
tgggcgcgtg ccttcgtgat cgaggaagcg ccagcggac gtcgcctggt ctacgtcaac      180
accgacctgg ggatgacctt ccaggccgtg cacctgaagg tcctggcccg gctcaaggcg     240
aagtaccccg gtgtctacga cgagaacaac gtgatgctcg ccgccaccca cacccactcc     300
ggtccgggcg gcttctccca ctacgcgatg tacaacctgt cggtgctcgg cttccaggaa     360
aagaccttca cgccatcgt cgacggcatc gtccgctcca tcgagcgggc ccaggccagg      420
ttgcagcccg gccgcctgtt ctacggcagc ggcgagctgc gcaacgccag ccgcaaccgt     480
tcgctgctgt cgcacctgaa gaatccggac atcgccggct acgaggatgg catcgacccg     540
cagatgagcg tgctcagctt cgtcgacgcc aacggcgagc tggccggcgc gatcagttgg     600
ttcccggtgc acagcacctc gatgaccaac gccaatcacc tgatctcccc ggacaacaag     660
ggctacgcct cctatcactg ggagcacgac gtcagccgca gagcggtttt cgtcgccgcc     720
ttcgcccaga ccaatgccgg caacctgtcg cccaacctga acctgaagcc cggctccggt     780
cccttcgaca acgagttcga caacacccgc gagatcggtc tgcgccaatt cgccaaggcc     840
tacgagatcg ccggccaggc ccaggaggaa gtgctcggcg aactggattc gcgcttccgt     900
ttcgtcgact tcacccgcct gccgatccgc ccggagttca ccgacggcca gccgcgccag     960
ttgtgcaccg cggccatcgg caccagcctg gccgccggta gcaccgaaga cggtccaggc    1020
ccgctggggc tggaggaagg caacaatccg ttcctctcgg cccttggcgg gttgctcacc    1080
ggcgtgccgc cgcaggaact ggtgcaatgc caggcggaaa agaccatcct cgccgacacc    1140
ggcaacaaga aaccctaccc ctggacgccg acggtgctgc cgatccagat gttccgcatc    1200
ggccagttgg aactgctcgg cgccccgcc gagttcaccg tgatggccgg ggtgcggatc    1260
cgccgcgcg tgcaggcggc cagcgaagcg ccggtatcc gccatgtggt cttcaatggc    1320
tacgcgaatg cctatgccag ctacgtcacc acccgcgagg aatacgccgc ccaggaatac    1380
gaaggcggct cgaccctcta cggccccctgg acccaggccg cctaccagca gttgttcgtc    1440
gacatggcgg tggcgctgcg cgaacgcctg ccggtggaaa cctcggcgat agcgccggac    1500
ctgtcctgct gccagatgaa cttccagacc ggagtagtgg ccgatgatcc ctatatcggc    1560
aagtccttcg gcgacgtgtt gcaacaaccc agggaaagtt atcgcatcgg cgacaaggtg    1620
accgtcgctt tcgtgaccgg acatccgaag aatgacttgc gcaccgagaa gactttcctg    1680
gaagtggtga atatcggcaa ggatggcaaa cagacgcccg tgaccgttgc caccgataat    1740
gactgggata cccaataccg ctgggagaga gtgggtatat ctgcctcgaa agcgactatc    1800
agctggtcca ttccaccagg gaccgagccc ggccattact acatcaggca ctatggcaac    1860
gcgaagaact tctggaccca gaagatcagc gaaatcggcg gctcgacccg ctccttcgag    1920
gtgctcggca ccactcccta g                                              1941
```

<210> SEQ ID NO 3
<211> LENGTH: 18
<212> TYPE: PRT
<213> ORGANISM: Pseudomonas aeruginosa

```
<220> FEATURE:
<223> OTHER INFORMATION: any n or Xaa = Unknown

<400> SEQUENCE: 3

Ser Phe Gly Asp Val Leu Gln Gln Pro Arg Glu Ser Tyr Arg Ile Gly
 1               5                  10                  15
Asp Lys

<210> SEQ ID NO 4
<211> LENGTH: 16
<212> TYPE: PRT
<213> ORGANISM: Pseudomonas aeruginosa
<220> FEATURE:
<223> OTHER INFORMATION: any n or Xaa = Unknown

<400> SEQUENCE: 4

Ile Ser Glu Ile Gly Gly Ser Thr Arg Ser Phe Glu Val Leu Gly Thr
 1               5                  10                  15

<210> SEQ ID NO 5
<211> LENGTH: 11
<212> TYPE: PRT
<213> ORGANISM: Pseudomonas aeruginosa
<220> FEATURE:
<223> OTHER INFORMATION: any n or Xaa = Unknown

<400> SEQUENCE: 5

Asp Asp Leu Pro Tyr Arg Phe Gly Leu Gly Lys
 1               5                  10

<210> SEQ ID NO 6
<211> LENGTH: 11
<212> TYPE: PRT
<213> ORGANISM: Pseudomonas aeruginosa
<220> FEATURE:
<223> OTHER INFORMATION: Position 3 = Xaa = Unknown
<220> FEATURE:
<223> OTHER INFORMATION: any n or Xaa = Unknown

<400> SEQUENCE: 6

Val Thr Xaa Ala Phe Val Thr Gly His Pro Lys
 1               5                  10

<210> SEQ ID NO 7
<211> LENGTH: 10
<212> TYPE: PRT
<213> ORGANISM: Pseudomonas aeruginosa
<220> FEATURE:
<223> OTHER INFORMATION: any n or Xaa = Unknown

<400> SEQUENCE: 7

Thr Phe Leu Glu Val Val Asn Ile Gly Lys
 1               5                  10

<210> SEQ ID NO 8
<211> LENGTH: 25
<212> TYPE: PRT
<213> ORGANISM: Pseudomonas aeruginosa
<220> FEATURE:
<223> OTHER INFORMATION: any n or Xaa = Unknown

<400> SEQUENCE: 8

Asp Asp Leu Pro Tyr Arg Phe Gly Leu Gly Lys Ala Asp Ile Thr Gly
 1               5                  10                  15
Glu Ala Ala Glu Val Gly Met Met Gly
                20                  25
```

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:Designed
      oligonucleotide based on the amino acid sequence
      represented in SEQ ID NO:5.
<220> FEATURE:
<223> OTHER INFORMATION: any n or Xaa = Unknown

<400> SEQUENCE: 9
gaygayctnc cntaymg                                                      17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:Designed
      oligonucleotide based on the amino acid sequence
      represented in SEQ ID NO:5.
<220> FEATURE:
<223> OTHER INFORMATION: any n or Xaa = Unknown

<400> SEQUENCE: 10
gaygayttrc cntaymg                                                      17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:Designed
      oligonucleotide based on the amino acid sequence
      represented in SEQ ID NO:3.
<220> FEATURE:
<223> OTHER INFORMATION: any n or Xaa = Unknown

<400> SEQUENCE: 11
ccratnckrt asgaytc                                                      17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:Designed
      oligonucleotide based on the amino acid sequence
      represented in SEQ ID NO:3.
<220> FEATURE:
<223> OTHER INFORMATION: any n or Xaa = Unknown

<400> SEQUENCE: 12
ccratnckrt agctytc                                                      17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:Designed
      oligonucleotide based on the amino acid
      represented in SEQ ID NO:3.
<220> FEATURE:
<223> OTHER INFORMATION: any n or Xaa = Unknown

<400> SEQUENCE: 13

```
gaygtsytsc arcarcc                                                      17

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:Designed
      oligonucleotide based on the amino acid sequence
      represented in SEQ ID NO:4.
<220> FEATURE:
<223> OTHER INFORMATION: any n or Xaa = Unknown

<400> SEQUENCE: 14
aagctycasr asccvtg                                                      17

<210> SEQ ID NO 15
<211> LENGTH: 670
<212> TYPE: PRT
<213> ORGANISM: Pseudomonas aeruginosa
<220> FEATURE:
<223> OTHER INFORMATION: any n or Xaa = Unknown

<400> SEQUENCE: 15
```

Met Ser Arg Ser Ala Phe Thr Ala Leu Leu Leu Ser Cys Val Leu Leu
 1               5                  10                  15

Ala Leu Ser Met Pro Ala Arg Ala Asp Asp Leu Pro Tyr Arg Phe Gly
                20                  25                  30

Leu Gly Lys Ala Asp Ile Thr Gly Glu Ala Ala Glu Val Gly Met Met
            35                  40                  45

Gly Tyr Ser Ser Leu Glu Gln Lys Thr Ala Gly Ile His Met Arg Gln
    50                  55                  60

Trp Ala Arg Ala Phe Val Ile Glu Glu Ala Ala Ser Gly Arg Arg Leu
65                  70                  75                  80

Val Tyr Val Asn Thr Asp Leu Gly Met Thr Phe Gln Ala Val His Leu
                85                  90                  95

Lys Val Leu Ala Arg Leu Lys Ala Lys Tyr Pro Gly Val Tyr Asp Glu
            100                 105                 110

Asn Asn Val Met Leu Ala Ala Thr His Thr His Ser Gly Pro Gly Gly
        115                 120                 125

Phe Ser His Tyr Ala Met Tyr Asn Leu Ser Val Leu Gly Phe Gln Glu
    130                 135                 140

Lys Thr Phe Asn Ala Ile Val Asp Gly Ile Val Arg Ser Ile Glu Arg
145                 150                 155                 160

Ala Gln Ala Arg Leu Gln Pro Gly Arg Leu Phe Tyr Gly Ser Gly Glu
                165                 170                 175

Leu Arg Asn Ala Ser Arg Asn Arg Ser Leu Leu Ser His Leu Lys Asn
            180                 185                 190

Pro Asp Ile Ala Gly Tyr Glu Asp Gly Ile Asp Pro Gln Met Ser Val
        195                 200                 205

Leu Ser Phe Val Asp Ala Asn Gly Glu Leu Ala Gly Ala Ile Ser Trp
    210                 215                 220

Phe Pro Val His Ser Thr Ser Met Thr Asn Ala Asn His Leu Ile Ser
225                 230                 235                 240

Pro Asp Asn Lys Gly Tyr Ala Ser Tyr His Trp Glu His Asp Val Ser
                245                 250                 255

Arg Lys Ser Gly Phe Val Ala Ala Phe Ala Gln Thr Asn Ala Gly Asn
            260                 265                 270

-continued

```
Leu Ser Pro Asn Leu Asn Leu Lys Pro Gly Ser Gly Pro Phe Asp Asn
            275                 280                 285

Glu Phe Asp Asn Thr Arg Glu Ile Gly Leu Arg Gln Phe Ala Lys Ala
        290                 295                 300

Tyr Glu Ile Ala Gly Gln Ala Gln Glu Val Leu Gly Glu Leu Asp
305                 310                 315                 320

Ser Arg Phe Arg Phe Val Asp Phe Thr Arg Leu Pro Ile Arg Pro Glu
                325                 330                 335

Phe Thr Asp Gly Gln Pro Arg Gln Leu Cys Thr Ala Ala Ile Gly Thr
            340                 345                 350

Ser Leu Ala Ala Gly Ser Thr Glu Asp Gly Pro Gly Pro Leu Gly Leu
        355                 360                 365

Glu Glu Gly Asn Asn Pro Phe Leu Ser Ala Leu Gly Gly Leu Leu Thr
    370                 375                 380

Gly Val Pro Pro Gln Glu Leu Val Gln Cys Gln Ala Glu Lys Thr Ile
385                 390                 395                 400

Leu Ala Asp Thr Gly Asn Lys Lys Pro Tyr Pro Trp Thr Pro Thr Val
                405                 410                 415

Leu Pro Ile Gln Met Phe Arg Ile Gly Gln Leu Glu Leu Leu Gly Ala
            420                 425                 430

Pro Ala Glu Phe Thr Val Met Ala Gly Val Arg Ile Arg Arg Ala Val
        435                 440                 445

Gln Ala Ala Ser Glu Ala Ala Gly Ile Arg His Val Val Phe Asn Gly
    450                 455                 460

Tyr Ala Asn Ala Tyr Ala Ser Tyr Val Thr Thr Arg Glu Glu Tyr Ala
465                 470                 475                 480

Ala Gln Glu Tyr Glu Gly Gly Ser Thr Leu Tyr Gly Pro Trp Thr Gln
                485                 490                 495

Ala Ala Tyr Gln Gln Leu Phe Val Asp Met Ala Val Ala Leu Arg Glu
            500                 505                 510

Arg Leu Pro Val Glu Thr Ser Ala Ile Ala Pro Asp Leu Ser Cys Cys
        515                 520                 525

Gln Met Asn Phe Gln Thr Gly Val Ala Asp Asp Pro Tyr Ile Gly
    530                 535                 540

Lys Ser Phe Gly Asp Val Leu Gln Gln Pro Arg Glu Ser Tyr Arg Ile
545                 550                 555                 560

Gly Asp Lys Val Thr Val Ala Phe Val Thr Gly His Pro Lys Asn Asp
                565                 570                 575

Leu Arg Thr Glu Lys Thr Phe Leu Glu Val Val Asn Ile Gly Lys Asp
            580                 585                 590

Gly Lys Gln Thr Pro Val Thr Val Ala Thr Asp Asn Asp Trp Asp Thr
        595                 600                 605

Gln Tyr Arg Trp Glu Arg Val Gly Ile Ser Ala Ser Lys Ala Thr Ile
    610                 615                 620

Ser Trp Ser Ile Pro Pro Gly Thr Glu Pro Gly His Tyr Tyr Ile Arg
625                 630                 635                 640

His Tyr Gly Asn Ala Lys Asn Phe Trp Thr Gln Lys Ile Ser Glu Ile
                645                 650                 655

Gly Gly Ser Thr Arg Ser Phe Glu Val Leu Gly Thr Thr Pro
            660                 665                 670

<210> SEQ ID NO 16
<211> LENGTH: 2013
<212> TYPE: DNA
```

<213> ORGANISM: Pseudomonas aeruginosa
<220> FEATURE:
<223> OTHER INFORMATION: any n or Xaa = Unknown

<400> SEQUENCE: 16

```
atgtcacgtt ccgcattcac cgcgctcttg ctgtcctgcg tcctgctggc gctctccatg      60
cctgccaggg ccgacgacct gccctaccgc ttcggcctgg gcaaggcgga catcaccggc     120
gaagccgccg aagtcggcat gatgggttac tcctccctcg aacagaagac cgccggcatc     180
cacatgcgcc agtgggcgcg tgccttcgtg atcgaggaag cggccagcgg acgtcgcctg     240
gtctacgtca acaccgacct ggggatgacc ttccaggccg tgcacctgaa ggtcctggcc     300
cggctcaagg cgaagtaccc cggtgtctac gacgagaaca acgtgatgct cgccgccacc     360
cacacccact ccggtccggg cggcttctcc cactacgcga tgtacaacct gtcggtgctc     420
ggcttccagg aaaagacctt caacgccatc gtcgacggca tcgtccgctc catcgagcgg     480
gcccaggcca ggttgcagcc cggccgcctg ttctacggca gcggcgagct gcgcaacgcc     540
agccgcaacc gttcgctgct gtcgcacctg aagaatccgg acatcgccgg ctacgaggat     600
ggcatcgacc cgcagatgag cgtgctcagc ttcgtcgacg ccaacggcga gctggccggc     660
gcgatcagtt ggttcccggt gcacagcacc tcgatgacca cgccaatca cctgatctcc      720
ccggacaaca agggctacgc ctcctatcac tgggagcacg acgtcagccg caagagcggt     780
ttcgtcgccg ccttcgccca gaccaatgcc ggcaacctgt cgcccaacct gaacctgaag     840
cccggctccg gtcccttcga caacgagttc gacaacaccc gcgagatcgg tctgcgccaa     900
ttcgccaagg cctacgagat cgccggccag gcccaggagg aagtgctcgg cgaactggat     960
tcgcgcttcc gtttcgtcga cttcacccgc ctgccgatcc gcccggagtt caccgacggc    1020
cagccgcgcc agttgtgcac cgcggccatc ggcaccagcc tggccgccgg tagcaccgaa    1080
gacggtccag gcccgctggg gctggaggaa ggcaacaatc cgttcctctc ggcccttggc    1140
gggttgctca ccggcgtgcc gccgcaggaa ctggtgcaat gccaggcgga aaagaccatc    1200
ctcgccgaca ccggcaacaa gaaacccctac ccctggacgc cgacggtgct gccgatccag    1260
atgttccgca tcggccagtt ggaactgctc ggcgccccg ccgagttcac cgtgatggcc     1320
gggggtgcgga tccgccgcgc ggtgcaggcg ccagcgaag cggccggtat ccgccatgtg    1380
gtcttcaatg gctacgcgaa tgcctatgcc agctacgtca ccacccgcga ggaatacgcc    1440
gcccaggaat acgaaggcgg ctcgaccctc tacgcccct ggaccaggc cgcctaccag      1500
cagttgttcg tcgacatggc ggtggcgctg cgcgaacgcc tgccggtgga aacctcggcg    1560
atagcgccgg acctgtcctg ctgccagatg aacttccaga ccggagtagt ggccgatgat    1620
ccctatatcg gcaagtcctt cggcgacgtg ttgcaacaac ccaggggaaag ttatcgcatc    1680
ggcgacaagg tgaccgtcgc tttcgtgacc ggacatccga agaatgactt gcgcaccgag    1740
aagactttcc tggaagtggt gaatatcggc aaggatggca acagacgcc cgtgaccgtt     1800
gccaccgata tgactgggga tacccaatac cgctgggaga gagtgggtat atctgcctcg    1860
aaagcgacta tcagctggtc cattccacca gggaccgagc ccggccatta ctacatcagg    1920
cactatggca acgcgaagaa cttctggacc cagaagatca gcgaaatcgg cggctcgacc    1980
cgctccttcg aggtgctcgg caccactccc tag                                 2013
```

<210> SEQ ID NO 17
<211> LENGTH: 21
<212> TYPE: DNA
<213> ORGANISM: Artificial Sequence

```
<220> FEATURE:
<223> OTHER INFORMATION: Description of Artificial Sequence: Primer 382U
<220> FEATURE:
<223> OTHER INFORMATION: any n or Xaa = Unknown

<400> SEQUENCE: 17
ggcttctccc actacgcgat g                                            21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Primer 884L
<220> FEATURE:
<223> OTHER INFORMATION: any n or Xaa = Unknown

<400> SEQUENCE: 18
cgaattggcg cagaccgatc t                                            21
```